US012376615B2

(12) United States Patent
Lee et al.

(10) Patent No.: US 12,376,615 B2
(45) Date of Patent: Aug. 5, 2025

(54) COMPOSITION FOR IMPROVING RESPIRATORY DISEASES USING LACTOBACILLUS PLANTARUM STRAIN

(71) Applicant: KOREA FOOD RESEARCH INSTITUTE, Iseo-myeon Wanju-gun Jeollabuk-do (KR)

(72) Inventors: So Young Lee, Jeonju-si Jeollabuk-do (KR); Seung Yong Kim, Jeonju-si Jeollabuk-do (KR); Young Do Nam, Jeonju-si Jeollabuk-do (KR); So Lim Park, Jeonju-si Jeollabuk-do (KR); Dong Uk Shin, Cheongju-si Chungcheongbuk-do (KR); Hee Soon Shin, Jeonju-si Jeollabuk-do (KR); Ji Eun Eom, Jeonju-si Jeollabuk-do (KR); Sun Young Jung, Dosan-ro Seo-gu Daejeon (KR); Dae Woon Choi, Taebaek-si Gangwon-do (KR)

(73) Assignee: KOREA FOOD RESEARCH INSTITUTE, Iseo-myeon Wanju-gun Jeollabuk-do (KR)

( * ) Notice: Subject to any disclaimer, the term of this patent is extended or adjusted under 35 U.S.C. 154(b) by 441 days.

(21) Appl. No.: 17/767,181

(22) PCT Filed: Oct. 8, 2020

(86) PCT No.: PCT/KR2020/013749
§ 371 (c)(1),
(2) Date: Apr. 7, 2022

(87) PCT Pub. No.: WO2021/071292
PCT Pub. Date: Apr. 15, 2021

(65) Prior Publication Data
US 2022/0369684 A1  Nov. 24, 2022

(30) Foreign Application Priority Data

Oct. 8, 2019 (KR) ......................... 10-2019-0124486
Oct. 8, 2019 (KR) ......................... 10-2019-0124489
Oct. 8, 2019 (KR) ......................... 10-2019-0124492

(51) Int. Cl.
*A23L 33/135* (2016.01)
*A61K 35/747* (2015.01)
*A61P 11/00* (2006.01)
*C12R 1/25* (2006.01)

(52) U.S. Cl.
CPC .......... *A23L 33/135* (2016.08); *A61K 35/747* (2013.01); *A61P 11/00* (2018.01); *C12R 2001/25* (2021.05)

(58) Field of Classification Search
CPC ... A23L 33/135; A23L 33/105; A61K 35/747; A61K 36/185; A61K 2236/33; A61K 2236/37; A61K 36/282; A61P 11/00; A61P 11/06; C12R 2001/25; C12R 2001/02; A23V 2002/00; A23V 2400/169
See application file for complete search history.

(56) References Cited

U.S. PATENT DOCUMENTS

2015/0240200 A1  8/2015  Tsai et al.
2019/0030097 A1  1/2019  Kim et al.

FOREIGN PATENT DOCUMENTS

| CN | 104996994 A | 10/2015 |
|---|---|---|
| CN | 106262931 A | 1/2017 |
| JP | 6729913 B2 | 7/2020 |
| KR | 1020130046897 A | 5/2013 |
| KR | 101485395 B1 | 1/2015 |
| KR | 1020160110232 A | 9/2016 |
| KR | 1020180123259 A | 10/2019 |
| WO | 2018191073 A1 | 10/2018 |

OTHER PUBLICATIONS

Hirose et al., Journal of Nutritional Science (2013), vol. 2, e39, p. 1-8; doi: 10.1017/jns.2013.35. (Year: 2013).*
Park et al., Journal of Medicinal Food, 17 (1) 2014, 6-20; DOI: 10.1089/jmf.2013.3083. (Year: 2014).*
Hong HJ, Kim E, Cho D, Kim TS. Differential suppression of heat-killed lactobacilli isolated from kimchi, a Korean traditional food, on airway hyper-responsiveness in mice. J Clin Immunol. May 2010;30(3):449-58. doi: 10.1007/s10875-010-9375-8. Epub Mar. 5, 2010. PMID: 20204477. (Year: 2010).*
"Types of wormwood, when to harvest, how to identify them, how to eat them, their benefits, and where they thrive." Apr. 8, 2002; https ://blog. naver.com/kjchol 123/221897530341.
Kim, S.-H. "Optimization of Ethanol Extraction Conditions for Artemisis capillaris Effective Components Using Response Surface Methodology." Journal of the Korean Society of Food Science and Nutrition. The Korean Society of Food Science and Nutrition. (May 31, 2014).
From the type of mugwort and the timing of collection, the method of distinguishing and eating, the efficacy, and the environment that grows well by type (Steel Herbs); https://blog.naver.com/kjcholl23/221897530341.
Jung et al., "Temperature impact on microbial and metabolic profiles in kimchi fermentation," Heliyon 10 (2024) e27174.
Kang et al., "Selection of Probiotic Bacteria from Yulmoo Kimchi Using a Stimulated Human Intestinal Model System," J. Korean Soc. Food Sci. Nutr. 41(3), 396-401 (2012).

(Continued)

*Primary Examiner* — Kade Ariani
(74) *Attorney, Agent, or Firm* — RAPHAEL BELLUM PLLC

(57) ABSTRACT

The present invention relates to a food composition for enhancing respiratory function and improving respiratory diseases, using *Lactobacillus plantarum* KF511 strain; a health functional food comprising the food composition; and a pharmaceutical composition for preventing or treating the respiratory diseases, comprising *Lactobacillus plantarum* strain, its culture solution, its concentrate, or its dried product, as an active ingredient.

8 Claims, 4 Drawing Sheets

Specification includes a Sequence Listing.

(56) References Cited

OTHER PUBLICATIONS

Murosaki et al., "Heat-killed Lactobacillus plantarum L-137 suppresses naturally fed antigen-specific IgE production by stimulation of IL-12 production in mice," J. Allergy Clin. Immunol. 57-64, Jul. 1998.

Fujiki et al., "Enhanced Immunomodulatory Activity and Stability in Simulated Digestive Juices of Lactobacillus plantarum L-137 by Heat Treatment," Biosci. Biotechnol. Biochem., 76(5), 918-922, 2012.

\* cited by examiner

[FIG. 1]
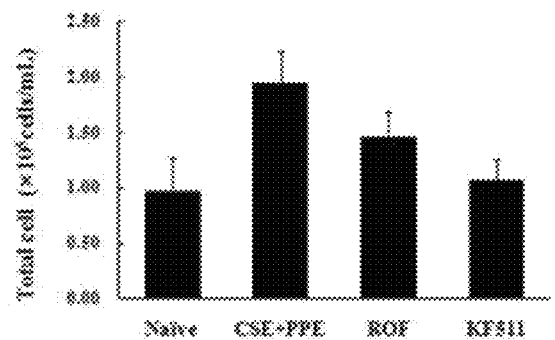
[FIG. 2]
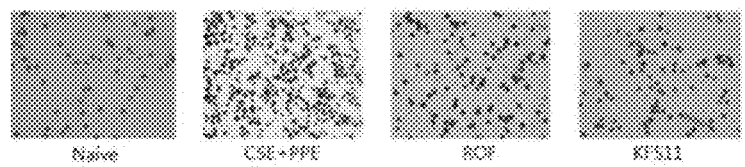
[FIG. 3]
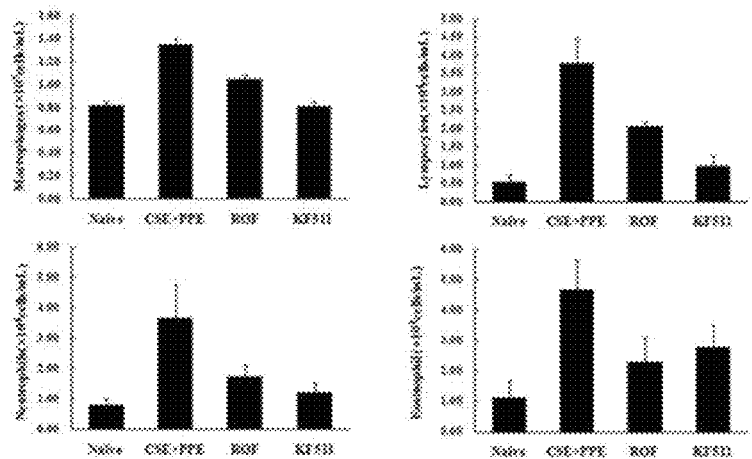

[FIG. 4]
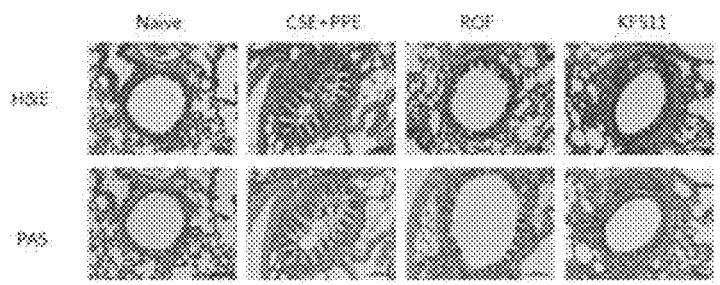
[FIG. 5]
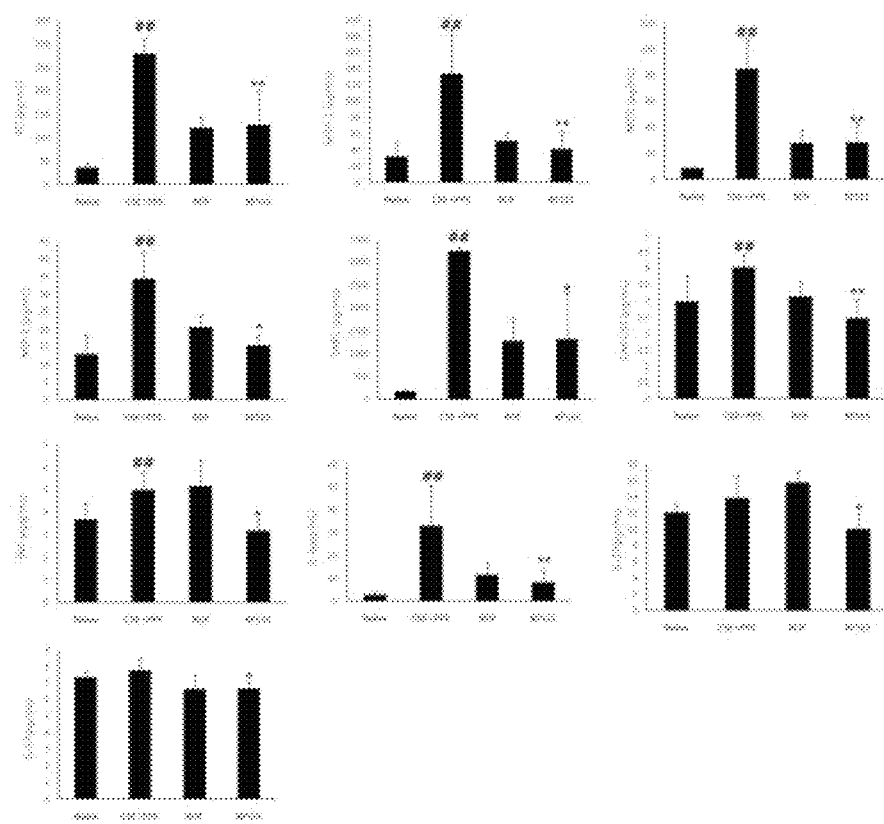

[FIG. 6]
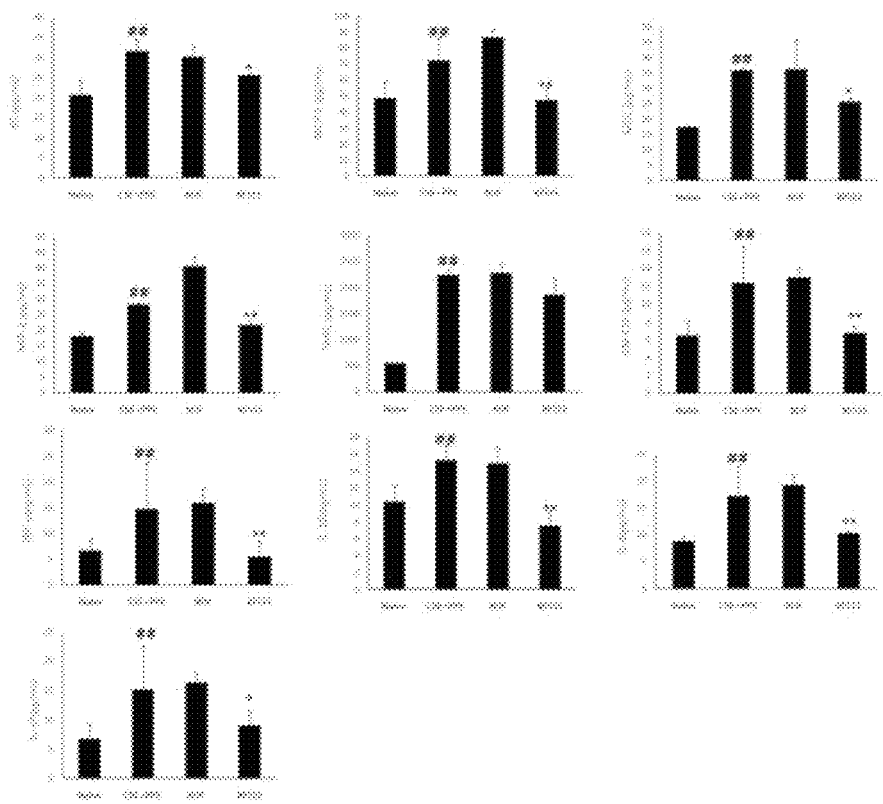
[FIG. 7]
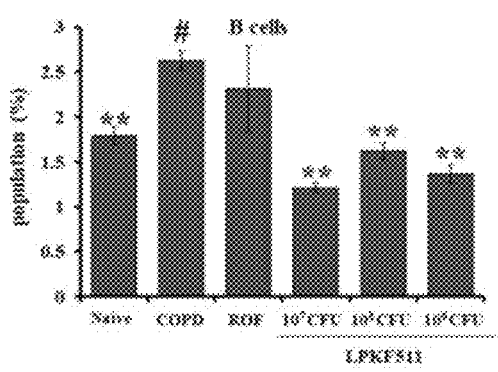

[FIG. 8]
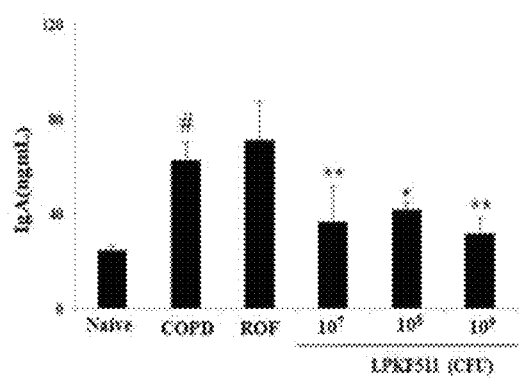
[FIG. 9]
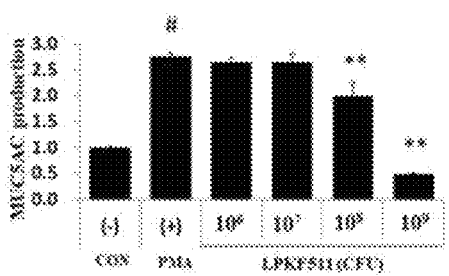

COMPOSITION FOR IMPROVING RESPIRATORY DISEASES USING LACTOBACILLUS PLANTARUM STRAIN

SEQUENCE LISTING

The Sequence Listing submitted herewith is an ASCII text file (2022-04-18_Sequence_Listing.txt, created on Apr. 18, 2022, 2526 bytes), is filed via EFS-Web, and is hereby incorporated by reference.

TECHNICAL FIELD

The present invention relates to a food composition for enhancing respiratory function and improving respiratory diseases, using *Lactobacillus plantarum* KF511 strain; a health functional food comprising the food composition; and a pharmaceutical composition for preventing or treating the respiratory diseases, comprising the *Lactobacillus plantarum* strain, its culture solution, its concentrate, or its dried product, as an active ingredient.

BACKGROUND ART

Bronchial asthma is an allergic disease characterized by reversible airway obstruction, airway hypersensitivity (increased airway resistance), mucus hypersecretion, and high IgE level in a serum. If TH2 (T helper 2) type immune cells stimulated by various antigens inhaled into an airway produce IL-4, 5, 13, etc., inflammatory cells such as T cells, eosinophils and mast cells are proliferated, differentiated, and activated to migrate to and infiltrate into the airway and tissues around the airway, causing chronic inflammatory diseases (J Clin Invest, 111: 291-297, 2003; N Engl J. Med. 2001; 44(5): 350-62; Toshio Hirano, Cytokine molecular biology, World Science, 2002). Therefore, one of the important targets for developing the therapeutic agent for asthma is to inhibit infiltration of the inflammatory cells such as the eosinophils.

A chronic obstructive pulmonary disease (COPD) is the chronic airway disease that shows cough, sputum, dyspnea, decreased expiratory flow rate, gas exchange disorder, etc., and is expected to become the third leading cause of human death by 2020, increasing worldwide every year (Am J Respir Crit Care Med, 2013, 187: 347-365; Am J Respir Crit Care Med, 2009, 180:396-406).

The COPD is developed by various causes such as smoking, air pollution, chemicals, occupational factors and genetic predisposition, and the smoking is the main cause of the COPD since 80% or more of the COPD patients have in fact been found to be smokers (Biol Pharm Bull, 2012, 35:1752-1760). The pathogenesis of the COPD includes inflammation, activation of proteolytic enzymes in a lung, oxidative stress, etc., and the cells that induce the inflammation are mainly neutrophils, macrophages and T lymphocytes. These inflammatory cells produce reactive oxygen species, various inflammatory cytokines, and various proteases that cause tissue damage (Korean Tuberculosis and Respiratory Sciences Association, Seoul: Gunja Publishing Company; 2007, p 301-5; Am J Respir Crit Care Med, 1997 155, 1441-1447; Am J Physiol Lung Cell Mol Physiol, 2010, 298: L262-L269). In particular, the neutrophils have been known to play an important role in pathogenesis of the COPD, because they cause lung damage by secreting substances such as elastases, collagenases, proteases such as MPO (myeloperoxidase), arachidonic acid metabolites (arachidonate), and reactive oxygen species (reactive oxygen free radical), to the outside of cells. Accordingly, the neutrophils are an important target in developing a therapeutic agent for the COPD (Am J Respir Cell Mol Biol, 2013, 48:531-539; Eur Respir J, 1998, 12:1200-1208).

In recent, it has been reported that Netosis activation of neutrophil extracellular traps is involved in the pathogenesis of the chronic lung/respiratory diseases including the COPD (PLoS One. 2014 May 15; 9(5): e97784); Respir Res. 2015 May 22; 16:59; J Immunol Res. 2017; 2017:6710278; Respirology. 2016 April; 21(3): 467-75).

Currently, bronchoalveolar lavage (BAL) is used as a means for examining the course of diseases such as the COPD and the asthma. In the bronchoalveolar lavage fluid (BALF), the inflammatory mediators such as inflammatory cytokines, reactive oxygen species, leukotrienes, and activation complements increase, and the neutrophils that account for less than 5% of the normal lung increase to the extent that they account for 80% of the total cells (Am J Respir Crit Care Med 154(1): 76-81, 1996).

There have been no reports of drugs that directly improve the COPD or the asthma so far. As the current therapeutic agent for the COPD or the asthma, bronchodilators (β2-agonists, anticholinergics, methylxanthines) and steroids (inhalation, oral) are mainly used to reduce a symptom and complication thereof.

DETAILED DESCRIPTION OF THE INVENTION

Technical Problem

A purpose of the present invention is to provide a food composition for enhancing respiratory function and improving respiratory diseases, comprising *Lactobacillus plantarum* KF511 strain, its culture solution, its concentrate, or its dried product, as an active ingredient; and a health functional food comprising the food composition.

Another purpose of the present invention is to provide a pharmaceutical composition for preventing or treating respiratory diseases, comprising *Lactobacillus plantarum* KF511 strain, its culture solution, its concentrate, or its dried product, as an active ingredient.

Technical Solution

The present invention will be described in detail as follows.

Each of the description and embodiment disclosed in the present application may also be applied to each of the other description and embodiment. That is, all the combinations of the various elements disclosed in the present application fall within the scope of the present application. Further, it cannot be considered that the scope of the present application is limited by the detailed description explained below.

The present inventors have completed the present invention by confirming that, as shown in the Examples and Experimental Examples below, *Lactobacillus plantarum* KF511 strain inhibits Netosis activation of neutrophil extracellular traps induced by phorbol myristate acetate (PMA), inhibits expression of inflammatory cytokines by Cigarette Smoke Extraction (CSE) of NCI-H292 cells that are a bronchial epithelial cell line, and furthermore, inhibits damage of a lung tissue in a mouse model of a respiratory disease induced by the CSE and PPE, inhibits infiltration of immune cells such as total cells, macrophages, lymphocytes, eosinophils, and neutrophils in BALF, and inhibits secretion of inflammatory cytokines and chemokines in the BALF and the lung tissue.

An aspect of the present invention for attaining the above purposes provides a food composition for enhancing respiratory function and improving respiratory diseases, comprising *Lactobacillus plantarum* KF511 strain, its culture solution, its concentrate, or its dried product, as an active ingredient; and a health functional food comprising the food composition.

As used herein, the term "*Lactobacillus plantarum*" refers to microorganisms of the genus *Lactobacillus* commonly found in various fermented foods and the intestinal tract of a human, and corresponds to gram-positive bacteria. The *Lactobacillus plantarum* has been known to have the largest genome among lactic acid bacteria, and has an appropriate pH of 3.4 to 8.8 and an appropriate temperature ranging from 12° C. to 40° C., which are required for growth and proliferation.

In the present invention, the *Lactobacillus plantarum* strain may be specifically "*Lactobacillus plantarum* KF511", and more concretely may be the one deposited under the accession number KCCM 12573P. The strain is isolated and identified from a fermented food, Kimchi, the medium composition for culturing the strain is a MRS medium, the culture condition includes a pH of 6.5±0.2, a temperature of 37° C. and a stirring culture for 24 hours, the oxygen demand is facultative anaerobic, and the strain can be preserved by a freeze-drying or freezing of the cell suspension. Meanwhile, the *Lactobacillus plantarum* KF511 strain of the present invention has a 16s rDNA sequence number (SEQ ID NO: 1) with a length of 1499 kb.

The *Lactobacillus plantarum* KF511 strain of the present invention has been deposited with the Korea Culture Center of Microorganisms (KCCM), located at Yurim B/D, 45 Hongjenae-2ga-gil, Seodaemun-gu, Seoul 03641, Republic of Korea, an international depositary authority under the Budapest Treaty, as of Aug. 21, 2019, and has been given an accession number of KCCM 12573P. The Deposits were made under the provisions of the Budapest Treaty on the International Recognition of the Deposit of Microorganisms for the Purposes of Patent Procedure. Further, these deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicant will make available to the public, pursuant to 37 C.F.R. § 1.808, sample(s) of the deposits. The deposits will be maintained in the KCCM depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. § 1.801-1.809, including providing an indication of the viability of the sample upon deposit.

As used herein, the term "culture solution" or "culture" refers to a medium containing by-products and strains generated through metabolism when the strains are cultured in the medium and ingest nutrients. Specifically, it may mean a culture solution or a culture of the *Lactobacillus plantarum* KF511 strain. Further, a concentrate or a dilution of the medium, a dried product obtained by drying the medium, a crude purified product or a purified product of the medium, or a mixture thereof may also be included as an active ingredient in the composition of the present invention.

In the present invention, the term "active ingredient" refers to a component that exhibits a desired activity alone, or a component capable of exhibiting activity together with a carrier that is not active on its own.

In the present invention, the term "enhancement of respiratory function" refers to any action that restores the function of respiratory organs such as a nasal cavity, a pharynx, a larynx, a trachea, a bronchus and a lung in their original healthy state, or that improves the function of the respiratory organs, which has been deteriorated due to symptoms caused by smoking, fine dust, activation of neutrophil Netosis, or other respiratory diseases, to their original healthy state.

Further, in the present invention, the term "respiratory diseases" refer to diseases caused in the respiratory organs of an individual, such as the nasal cavity, the pharynx, the larynx, the trachea, the bronchus and lung. Specifically, the respiratory diseases may mean those caused by the smoking or the fine dust; or a pulmonary disease accompanied by Netosis, but is not particularly limited thereto. More specifically, the respiratory diseases may refer to a pulmonary disease accompanied by symptoms of sputum, dyspnea, airway hypersensitivity, airway obstruction, mucus hypersecretion, decreased expiratory flow rate and/or gas exchange disorder, and more specifically, may mean one or more selected from the group consisting of asthma, chronic obstructive pulmonary disease (COPD), tracheitis, bronchitis, diffuse interstitial pulmonary disease, acute respiratory distress syndrome (ARDS), acute lung injury, cystic fibrosis, bronchiolitis, influenza virus infection, pneumonia, tuberculosis and transfusion-related acute lung injury, and most specifically, may refer to the asthma or the COPD.

The composition of the present invention may comprise the active ingredient in any amount (effective amount) according to its specific use, formulation, purpose of blending, etc., as long as the active ingredient can enhance the respiratory function and have activity of improving, preventing, or treating the respiratory diseases. The typical effective amount can be determined within the range of 0.001 wt % to 20.0 wt %, based on the total weight of the composition. The "effective amount" refers to an amount of the active ingredient included in the composition of the present invention that can exhibit the intended functional and pharmacological effects, such as enhancing the respiratory function and improving, preventing or treating the respiratory diseases, in particular the improved effects of the asthma or the COPD, when the composition of the present invention is administrated to a subject to be applied according to the suggestion of a person who has an ordinary skill in the art during the administration period. Such an effective amount can be determined empirically by a person who has an ordinary skill in the art within the scope of his/her ability.

The subject to which the composition of the present invention can be applied may be a mammal such as a dog, a cat, a cow, a horse, a pig or a human, and the human may be preferable.

The food composition of the present invention may comprise *Lactobacillus plantarum* KF511 having the number of $10^1$ to $10^{12}$ CFU bacteria, preferably the number of $10^6$ to $10^{12}$ CFU bacteria, as an active ingredient.

Further, in addition to the active ingredient, in order to enhance the convenience of taking or ingesting the composition through addition of similar activities such as anti-inflammatory activity, anti-allergic activity, etc., the composition of the present invention may additionally comprise any compound or natural extract whose safety has already been verified in the art and known to have the corresponding activities.

Such a compound or extract may include compounds or extracts listed in the official compendium such as the pharmacopeias of each country ('Korean Pharmacopoeia' in Korea) and the health functional food ordinances of each country ('Health functional food standard and specification' announced by the Ministry of Food and Drug Safety in Korea); compounds or extracts that have been approved for items in accordance with the laws of each country that regulate the manufacture and sale of pharmaceuticals ('Pharmaceutical law' in Korea); and compounds or extracts whose functionality has been recognized in accordance with the laws of each country that regulate the manufacture and sale of a health functional food ('Health Functional Food Act' in Korea). For example, the compound or extract includes, without any particular limitation, dimethylsulfonylmethane (MSM), N-acetylglucosamine, etc., approved for anti-inflammatory function in accordance with the 'Health Functional Food Act' in Korea; and a complex of *Enterococcus faecalis* heat-treated dry powder, guava leaf extract, etc., a complex of *Actinidia* extract, leaflet extract, picaopreto powder, etc., or 1-palmitoyl-2-linoleoyl-3-acetyl-rac-glycerol (PLAG), etc., that have been approved for anti-allergic function. The composition of the present invention may comprise one or more of these compounds or natural extracts together with the active ingredient.

In a specific aspect, the composition of the present invention may be identified as a food composition, wherein the food includes a health functional food.

As used herein, the term "health functional food" refers to a food manufactured and processed in the form of a tablet, a capsule, powder, granule, liquid, a pill, etc., using raw materials or ingredients with useful functionality for the human body. The "functionality" means to obtain a useful effect for health purposes such as controlling of nutrients or physiological action with respect to the structure and function of the human body. The health functional food of the present invention can be prepared in accordance with the method used in the art normally by adding raw materials and ingredients commonly added in the art. Also, a formulation of the health functional food may be manufactured without any limitation as long as it is recognized as the health functional food. The food composition of the present invention can be prepared in various forms. Unlike the general drugs, it has the advantage of not having a side effect that may occur during long-term ingestion of the drugs by using the food as a raw material, and has an excellent portability. The health functional food of the present invention can be taken as a supplement to increase improvement effect of the asthma or the COPD, and further enhance the respiratory function and increase improvement effect of the respiratory diseases.

The food composition of the present invention may be prepared in any form, for example, beverages such as a tea, a juice, a carbonated drink and an ionic beverage, processed milks such as a milk and a yogurt, foods such as a gum, a rice cake, a Korean traditional cookie, a bread, confectionery and a noodle, and formulations of the health functional food such as a tablet, a capsule, a pill, granule, liquid, powder, a flake, a paste, a syrup, a gel, a jelly and a bar. In addition, the food composition of the present invention may have any product classification in terms of the legal and functional classification as long as it conforms to the enforcement law at the time of manufacturing and distribution. For example, it may be the health functional food according to the 'Health Functional Food Act' of Korea, or confectionery, beans, tea, beverages and special purpose foods, etc., according to each food type under the Food Ordinance of the Korea 'Food Sanitation Act' ('Food Standards and Specifications' announced by the Ministry of Food and Drug Safety).

Further, the food composition of the present invention may comprise food additives in addition to the active ingredient. In general, the food additives may be considered to be substances that are added to the food and mixed with or infiltrated into the food in manufacturing, processing, or preserving the food. Since the food additives are consumed daily for a long time with the food, their safety must be guaranteed. According to the laws of each country that regulates the manufacture and distribution of the food ('Food Sanitation Act' in Korea), the Food Additives Ordinance is limitedly provided in terms of ingredients and function of the food additives whose safety is guaranteed. In the Korean Food Additives Ordinance ("Food Additive Standards and Specifications" announced by the Ministry of Food and Drug Safety), the food additives are classified into a chemically synthetic product, a natural additive, and a mixed preparation in terms of their ingredients, and are classified into a sweetener, a flavoring agent, a preservative, an emulsifier, an acidulant, a thickener, etc., in terms of their function.

The sweetener is used to impart an appropriate sweetness to the food, and may include a natural or synthetic sweetener. The natural sweetener is preferably used, and may include a sugar sweetener such as a corn syrup solid, a honey, sucrose, fructose, lactose, and maltose.

The flavoring agent is used to improve taste or flavor, and may include both of natural and synthetic flavoring agents. The natural flavoring agent is preferably used. Using the natural flavoring agent can serve the purpose of enhancing nutrition in addition to the flavor. The natural flavoring agent may be obtained from an apple, a lemon, a tangerine, a grape, a strawberry, a peach, or the like, or be obtained from a green tea leaf, Solomon's seal, a bamboo leaf, a cinnamon, a chrysanthemum leaf, a jasmine, and the like. In addition, the natural flavoring agent may be obtained from a ginseng (a red ginseng), a bamboo shoot, an aloe vera, a ginkgo, and the like. The natural flavoring agent may be a liquid concentrate or a solid extract. In some cases, the synthetic flavoring agent may be used and include ester, alcohol, aldehyde, terpene, and the like.

The preservative may include calcium sorbate, sodium sorbate, potassium sorbate, calcium benzoate, sodium benzoate, potassium benzoate, EDTA (ethylenediaminetetraacetic acid), etc., and the emulsifier may include acacia gum, carboxymethyl cellulose, xanthan gum, pectin, and the like. The acidulant may include citric acid, malic acid, fumaric acid, adipic acid, phosphoric acid, gluconic acid, tartaric acid, ascorbic acid, acetic acid, and the like. The acidulant may be added such that the food composition has an appropriate acidity for the purpose of inhibiting the growth of microorganisms in addition to enhancing the taste.

The thickener may include a suspending agent, a settling agent, a gel-forming agent, a bulking agent, and the like.

The food composition of the present invention may contain, in addition to the food additives described above, physiologically active substances or minerals known in the art for the purpose of supplementing and reinforcing the functionality and the nutrition and guarantying stability as the food additives. The physiologically active substances may include catechins contained in the green tea, vitamins such as vitamin B1, vitamin C, vitamin E, and vitamin B12, tocopherol, dibenzoylthiamine, and the like. The minerals may include a calcium preparation such as calcium citrate, a magnesium preparation such as magnesium stearate, an iron preparation such as iron citrate, chromium chloride, potassium iodide, selenium, germanium, vanadium, zinc, etc.

The food composition of the present invention may contain the above food additives in an appropriate amount to achieve its purpose depending on the type of a product. For the other food additives that may be included in the food composition of the present invention, reference may be made to the Food Ordinance or the Food Additives Ordinance of each country.

Another aspect of the present invention for achieving the above purpose is to provide a pharmaceutical composition for preventing or treating respiratory diseases, comprising *Lactobacillus plantarum* KF511 strain, its culture solution, its concentrate, or its dried product, as an active ingredient. The terms of *Lactobacillus plantarum, Lactobacillus plantarum* KF511, culture solution, active ingredient and respiratory diseases are the same as described above.

As used herein, the term "preventing" refers to any act of suppressing or delaying symptoms of respiratory diseases of an individual by administrating the composition comprising the culture solution of the *Lactobacillus plantarum* KF511 strain according to the present invention.

As used herein, the term "treating" refers to any action of improving or curing symptoms of respiratory diseases of an individual by administrating the composition comprising the culture solution of the *Lactobacillus plantarum* KF511 strain according to the present invention.

The pharmaceutical composition of the present invention may comprise the *Lactobacillus plantarum* KF511 having the number of $10^1$ to $10^{12}$ CFU bacteria, preferably $10^6$ to $10^{12}$ CFU bacteria, as an active ingredient.

The pharmaceutical composition of the present invention comprising a pharmaceutically acceptable carrier thereof in addition to the active ingredient may be prepared as an oral formulation or a parenteral formulation according to the route of administration by a conventional method known in the art. Specifically, the route of administration may be any suitable route including topical route, oral route, intravenous route, intramuscular route, and direct absorption through a mucosal tissue, and may be used in combination of two or more routes. An example for the combination of two or more routes is the case in which two or more formulations of drugs are combined according to the route of administration. For example, one drug is first administered by the intravenous route and the other drug is secondarily administered by the topical route.

The pharmaceutically acceptable carrier is well known in the art depending on the route of administration or the formulation, and specifically, reference may be made to the pharmacopeias of each country, including the 'Korean Pharmacopoeia'.

In case the pharmaceutical composition of the present invention is prepared as the oral formulation, it may be made as the formulation such as powder, granule, a tablet, a pill, a dragee tablet, a capsule, liquid, a gel, a syrup, suspension, wafer, etc., together with a suitable carrier, according to the method known in the art. In this case, the suitable carrier include sugars such as lactose, glucose, sucrose, dextrose, sorbitol, mannitol and xylitol, starches such as corn starch, potato starch and wheat starch, celluloses such as methylcellulose, ethylcellulose, sodium carboxymethylcellulose or hydroxypropylmethylcellulose, polyvinylpyrrolidone, water, methylhydroxybenzoate, propylhydroxybenzoate, magnesium stearate, a mineral oil, a malt, a gelatin, a talc, a polyol, a vegetable oil, ethanol, glycerol etc. The formulation may contain an appropriate binder, a lubricant, a disintegrant, a colorant, a diluent, etc., if necessary. The suitable binder includes a starch, magnesium aluminum silicate, a starch paste, a gelatin, methylcellulose, sodium carboxymethylcellulose, polyvinylpyrrolidone, glucose, a corn sweetener, sodium alginate, polyethylene glycol, a wax, and the like. The lubricant includes sodium oleate, sodium stearate, magnesium stearate, sodium benzoate, sodium acetate, sodium chloride, silica, talcum, stearic acid, a magnesium salt and calcium salt thereof, polyethylene glycol, etc. The disintegrant includes a starch, methyl cellulose, an agar, a bentonite, a xanthan gum, alginic acid or a sodium salt thereof. Also, the diluent includes lactose, dextrose, sucrose, mannitol, sorbitol, cellulose, glycine, etc.

In case the pharmaceutical composition of the present invention is prepared as the parenteral formulation, it may be formulated in the form of an injection, a transdermal administration, a nasal inhalant and a suppository together with a suitable carrier according to the method known in the art. When formulated as the injection, the suitable carrier includes an aqueous isotonic solution or a suspension, and specifically, phosphate buffered saline (PBS) or sterile water for injection containing triethanolamine, or an isotonic solution such as 5% dextrose. When formulated as the transdermal administration, it may be formulated in the form of an ointment, a cream, a lotion, a gel, an external solution, a pasta agent, a liniment agent, an aerosol, and the like. When formulated as the nasal inhalant, it may be formulated in the form of an aerosol spray using a suitable propellant such as dichlorofluoromethane, trichlorofluoromethane, dichlorotetrafluoroethane, carbon dioxide, and the like. When formulated as the suppository, the carrier includes witepsol, tween 61, polyethylene glycol, a cacao butter, a laurin fat, polyoxyethylene sorbitan fatty acid ester, polyoxyethylene stearate, sorbitan fatty acid ester, etc.

The Specific formulation of the pharmaceutical composition is known in the art, and is referenced in, for example, Remington's Pharmaceutical Sciences (19th ed., 1995). This document is regarded as a part of this specification.

A preferred dosage of the pharmaceutical composition of the present invention is in the range of 0.001 mg/kg to 10 g/kg per a day, preferably 0.001 mg/kg to 1 g per a day, depending on condition, weight, sex, age, severity of the patient, and a route of administration. The dosage may be performed once a day or divided into several times a day. Such dosages should not be construed to limit the scope of the present invention in any way.

Advantageous Effects

According to the present invention, *Lactobacillus plantarum* KF511 strain shows activities of inhibiting secretion of MUC5AC in a mucus hypersecretion model using a respiratory epithelial cell (H292) of a human, inhibiting Netosis activation of neutrophil extracellular traps, inhibiting expression of inflammatory cytokines by Cigarette Smoke Extraction (CSE) of NCI-H292 cells that are a bronchial epithelial cell line, and furthermore, inhibiting damage of a lung tissue in a mouse model of a respiratory disease induced by the CSE and PPE, inhibiting infiltration of immune cells such as total cells, macrophages, lymphocytes, eosinophils, and neutrophils in BALF, and inhibiting secretion of inflammatory cytokines and chemokines in the BALF and the lung tissue.

BRIEF DESCRIPTION OF THE DRAWINGS

FIG. 1 shows the total number of cells counted from bronchoalveolar lavage fluid (BALF) after administrating the *Lactobacillus plantarum* KF511 strain of the present invention and ROF as a positive control to a respiratory disease (COPD) mouse model induced by PPE/CSE.

FIGS. 2 and 3 show the results of analyzing immune cells (macrophage, lymphocyte, neutrophil and eosinophil) in BALF through Diff-Quick staining.

FIG. 4 shows the results of staining lung tissues extracted from a respiratory disease (COPD) mouse model.

FIG. 5 shows the results of analyzing cytokines and chemokines (KC, MCP-1, MDC, MIP-2, TARC, GM-CSF, INF-gamma, IL-6, IL-10, IL-17) in BALF of a respiratory disease (COPD) mouse model.

FIG. 6 shows the results of analyzing cytokines and chemokines (KC, MCP-1, MDC, MIP-2, TARC, GM-CSF, INF-gamma, IL-1beta, IL-6, IL-17) from lung tissues of a respiratory disease (COPD) mouse model.

FIG. 7 shows the results of measuring ratios of B cells in lung tissues after treating the *Lactobacillus plantarum* KF511 strain to the lung tissues derived from a respiratory disease (COPD) mouse model for each concentration.

FIG. 8 shows the results of measuring IgA contents in BALF after treating the *Lactobacillus plantarum* KF511 strain to a respiratory disease (COPD) mouse model for each concentration.

FIG. 9 shows the results of measuring expression levels of MUC5AC after treating the *Lactobacillus plantarum* KF511 strain to NCI-H292 cells, a mucinous epithelial cancer cell line of human respiratory epithelial cells, for each concentration.

DETAILED DESCRIPTION OF THE EMBODIMENTS

Hereinafter, the present invention will be described in more detail through the following Examples. However, these Examples are intended to illustrate the present invention only, and not to limit the scope of the present invention to these Examples.

Example 1: Isolation and Identification of *Lactobacillus plantarum* KF511 Strain

*Lactobacillus plantarum* strain according to the present invention was isolated from Kimhi that is traditionally prepared using *Lactobacillus* MRS agar medium (MRS medium, BD288130, Difco Company, USA), and the isolated strain was identified through 16S rDNA sequencing. As a result of the identification, the 16s rDNA base sequence (SEQ ID NO: 1) of the strain showed a homology of 99.93% with the existing *Lactobacillus plantarum* ATCC14917(T) strain. The medium composition for culturing the strain is a MRS medium, the culture condition includes a pH of 6.5±0.2, a temperature of 37° C. and a stirring culture for 24 hours, the oxygen demand is facultative anaerobic, and the strain can be preserved through a freeze-drying or a freezing of the cell suspension.

The present inventors have named the above strain as *Lactobacillus plantarum* KF511. This strain has been deposited with the Korea Microorganism Conservation Center (KCCM), an international microbial depository authority, on Aug. 21, 2019, and has been given an accession number KCCM 12573P.

Experimental Example 1: PPE+CSE-Induced Respiratory Disease (COPD) Mouse Model

BALB/C mouse (male, 5 weeks old) were purchased from Orient Bio Company, acclimatized for 1 week, and grouped into n=10. The sample treatment group was orally administered with a sample of $10^7$ to $10^9$ CFU/head for 24 days from one week before the start of COPD induction until dissection, and the same amount of PBS was administered to the naive and COPD groups. At this time, the Roflumilast (ROF) group, the positive control group, was orally administered in a concentration of 10 mg/kg every day after the start of induction. For the COPD induction, 1.2 unit of Porcine Pancreatic Elastase (PPE) and 100% Cigarette Smoke Extraction (CSE) were used. 1.2 unit of the PPE was injected intranasally for a total of 3 times once every 7 days, and 20 μl of CSE was treated intranasally for 3 days from the next day after the PPE injection. After the last PPE injection, the dissection was performed the next day without treatment of the CSE. The dissection was performed after anesthesia with isoflurane using an inhalation anesthetic machine. During the period of experiment, a feed and a drinking water were provided in the form of self-feeding, and the groups were bred under the condition of 24° C. and 60% humidity.

Experimental Example 2: Total Number of Cells Infiltrated in BALF and Analysis of Immune Cells in BALF Through Diff-Quick Staining 2-1: Total Number of Cells Infiltrated in BALF After injecting 1 mL of a PBS through the airway of a respiratory disease (COPD) model mouse, 700 μL of bronchoalveolar lavage fluid (BALF) was recovered by gently massaging. 10 uL of the recovered BALF solution was mixed with Accustain T solution in the same amount, and 12 uL of the mixed solution was injected into an Accuchip channel. Thereafter, total cells were automatically counted with a cell counter (ADAM-MC, NANOENTEK. INC, Korea) (FIG. 1).

2-2: Analysis of Immune Cells in BALF Through Diff-Quick Staining

The recovered BALF was separated into a supernatant and a cell pellet through centrifugation under the condition of 300×g and 5 minutes. The cell pellet was resuspended by adding 700 μL of the PBS, and 150 μL of this BALF suspension was centrifuged with a Cytospin device (Centrifuge 5403, Eppendorf, Hamburg, Germany) under the condition of 1000 rpm, 10 minutes and 4° C. to attach the BALF cells on a slide. Thereafter, the cells were stained using a Diff-Quick staining reagent according to the protocol of the manufacturer (1-5-1 Wakinohamakaigandori, chuo-ku, Kobe, Japan), and then observed with a microscope (FIGS. 2 and 3).

Experimental Example 3: Histological Examination

A lung tissue was removed from the dissected respiratory disease (COPD) model mouse, and a mesenchyme of the lung was removed followed by fixed in 10% neutral buffered formalin for 3 days. The fixed tissue was dehydrated with ethyl alcohol and xylene, embedded in a paraffin, trimmed, and sliced to a thickness of 5 μm. After attaching the prepared section to a slide, it was stained with H&E to confirm its general shape, and then observed with a microscope (FIG. 4).

Experimental Example 4: Analysis of Cytokines and Chemokines in BALF

After injecting 1 mL of PBS through the airway of a respiratory disease (COPD) model mouse, 700 μL of bronchoalveolar lavage fluid (BALF) was recovered by gently massaging. The recovered BALF was centrifuged under the condition of 300×g and 5 minutes to separate a supernatant, and then used to analyze cytokines and chemokines (KC, MCP-1, MDC, MIP-2, TARC, GM-CSF, INF-gamma, IL-6, IL-10, IL-17). After taking 30 uL of the supernatant for the analysis of cytokines and chemokines, the experiment was performed according to the protocol of the manufacturer (Quansis Biosciences Company) of a Q-plex ELISA array kit. The results were shown for each of the cytokines or the chemokines in FIG. 5.

Experimental Example 5: Analysis of Cytokines and Chemokines in Lung Tissue

To a lung tissue of a respiratory disease (COPD) model mouse, a PBS was added in an amount corresponding to 10 times the weight of the lung tissue, crushed with a homogenizer, and centrifuged under the condition of 12,000 rpm and 20 min. The recovered supernatant was used to analyze cytokines and chemokines (KC, MCP-1, MDC, MIP-2, TARC, GM-CSF, INF-gamma, IL-1beta, IL-6, IL-17). After taking 30 uL of the supernatant for the analysis of cytokines and chemokines, the experiment was performed according to the protocol of the manufacturer (Quansis Biosciences Company) of a Q-plex ELISA array kit. The results were shown for each of the cytokines or the chemokines in FIG. 6.

Experimental Example 6: Measurement of a Ratio of Immune Cells in Lung Tissue

A lung tissue was recovered from a respiratory disease (COPD) model mouse, and minced using dissecting scissors. The sliced lung tissues were put into a GentleMACS C tube, and were treated with enzymes D and A according to the protocol of the manufacturer (Miltenyi Biotec Company) to unicellularize the tissues with a MACS dissociator. After the unicellularized cells were subjected to red blood cell lysis, the number of cells in each of the groups was measured. The cells were made in a concentration of $1 \times 10^7$ cells/mL, and 200 μL per well was dispensed in a 96-well V-bottom plate.

Before staining immune cell-related surface markers, Fc Block™ was treated with 0.8 μL/20 μL/well using a FACS buffer (PBS+8% $NaHCO_3$+1% FBS+10% $NaN_3$), and then pipetted and left in a refrigerate at 4° C. for 15 minutes. For washing, the supernatant was removed by centrifugation at 1800 rpm for 3 minutes. In order to stain the surface markers of various immune cells, related antibodies were calculated according to the recommended amount of a staining concentration from the manufacturer (Biolegend Company), respectively, and prepared by diluting in the FACS buffer.

The experiment was performed to use FITC anti-mouse I-A/I-E, PE anti-mouse CD11c, PerCP/Cy5.5 anti-mouse Ly-6C antibody, APC anti-mouse CD64 (FcγRI), Alexa Fluor 700 anti-mouse Ly-6G, APC/Fire 750 anti-mouse CD45 antibody, Brilliant Violet 421 anti-mouse CD24, and Brilliant Violet 510 anti-mouse/human CD11b antibody. The diluted antibodies were treated with 20 μL/well and reacted at a room temperature for 30 minutes. Then, they were washed with a PBS, and the cells were suspended in the PBS. The suspended cells were analyzed using Cytoflex (Beckman Coulter Company), a flow cytometer. The results were shown in FIG. 7 according to the treatment concentration of each *Lactobacillus plantarum* KF511 (LPKF511) strain.

Experimental Example 7: Measurement of IgA Content in BALF

IgA was measured according to the experimental method of the ELISA kit (eBioscience, USA). A capture antibody was diluted with a coating buffer, and 100 μl per well was dispensed into a 96-well Immunoplate, and then left at 4° C. for about a day. The next day, after washing twice using a washing buffer, a blocking buffer was dispensed in an amount of 250μ per well and left at a room temperature for 2 hours. After ending the blocking process followed by washing 4 times, the standard sample and the BALF solution of each group were diluted with an assay buffer, dispensed in an amount of 100μ per well, and left at the room temperature for 2 hours. After washing the solution 4 times, a detection-antibody was diluted with the assay buffer, dispensed in an amount of 100 μL per well, and left at the room temperature for 1 hour. After washing the solution 4 times, a substrate solution was dispensed in an amount of 100 μL per well and left at the room temperature for 15 minutes, and a stop solution was added in an amount of 100 μL per well to terminate the reaction. Thereafter, an absorbance was measured at a wavelength of 450 nm and quantified by a standard curve using Standard. The results were shown in FIG. 8 according to the treatment concentration of each *Lactobacillus plantarum* KF511 (LPKF511) strain.

Experimental Example 8: Confirmation of MUC5AC Inhibitory Ability Using NCI-H292 Cells Mucin, a glycoprotein in mucus, is produced by a mucin gene, and in particular, expression of MUC5AC, secretory mucin, plays an important role in the respiratory region. Accordingly, this experiment was performed to confirm inhibitory ability of MUC5AC of *Lactobacillus plantarum* KF511 strain using NCI-H292 cells, a mucinous epithelial cancer cell line of human respiratory epithelial cells.

8-1: Culture of H292 Cells

H292 cells were cultured to use RPMI 1640 medium containing 10% Fetal bovine serum (FBS), 100 unit/ml of penicillin and 100 mg/ml of streptomycin. The H292 cells were inoculated in a 48-well cell culture plate in a concentration of $4 \times 10^4$ cells/well, and cultured for 24 hours under the condition of providing 5% carbon dioxide ($CO_2$) at 37° C. After culturing for 24 hours, the culture medium was replaced with a medium in which a concentration of the FBS was lowered to 0.2%, and starvation was performed for 24 hours under the condition of providing 5% carbon dioxide ($CO_2$) at 37° C. Thereafter, all of the sample and a stimulant were treated to use a RPMI1640 medium without addition of a serum. A PMA (Phorbol 12-myristate 13-acetate) was used as the stimulant, and the final concentration was made to become 2 ng/mL, co-treated with KF511 $10^{6-9}$ cells/well, and cultured for 24 hours. A culture supernatant was recovered and used to measure MUC5AC by an ELISA analysis method.

8-2: Measurement of MUC5AC

The culture supernatant was dispensed into a 96-well immunoplate by 100 μL, dried in a dry oven at 50° C., and washed 3 times with a PBS to which 0.05% tween 20 was added. Thereafter, the same washing method as above was used between all the steps. 1% bovine serum albumin (BSA) was dispensed in an amount of 200 μL per well, and blocking was performed for 1 hour followed by being washed. MUC5AC antibody (abcam) was diluted 500-fold, dispensed in an amount of 100 μL per well, and reacted for 2 hours. After washing, a goat anti-mouse IgG HRP (abcam)

was diluted 2000-fold, dispensed in an amount of 100 μL per well, and then reacted for 1 hour after blocking light. A substrate solution (BD) was dispensed in an amount of 100 μL per well, and then reacted for 30 minutes after blocking the light, followed that the reaction was stopped by adding a stop solution in an amount of 50 μL per well. An absorbance was measured at 450 nm using an ELISA reader. An inhibitory ability of MUC5AC showed a degree of inhibition during sample treatment compared to a production ability of MUC5AC by a PMA, based on untreated control cells.

It was confirmed from the production ability of MUC5AC that the PMA increased production of MUC5AC by 2.5 times compared to the control cells that were not stimulated. In contrast, when the *Lactobacillus plantarum* KF511 (LPKF511) strain was treated, it was confirmed that the production of MUC5AC was significantly reduced depending on the treatment concentration thereof (FIG. 9).

From the above description, a person who has an ordinary knowledge in the technical field to which the present invention pertains will understand that the present invention can be embodied in other certain embodiments without changing the technical spirit or essential features thereof. In this regard, it should be understood that the Examples described above are intended to be illustrative and not to be restrictive in all respects. It should be construed that the scope of the present invention includes all changes or modifications derived from the meaning and scope of the claims described below, and equivalents thereof, rather than the above detailed descriptions.

What are claimed are:

1. A food composition for enhancing respiratory function and improving respiratory diseases, comprising:

Lactobacillus plantarum KF511 strain (*L. plantarum* KF511);
a culture solution comprising *L. plantarum* KF511;
a concentrate comprising *L. plantarum* KF511; or
a dried product comprising *L. plantarum* KF511;
wherein the food composition comprises $10^7$ to $10^{12}$ CFU of the *L. plantarum* KF511, the *L. plantarum* KF511 is an active ingredient in the food composition and is assigned an accession number KCCM 12573P.

2. The food composition according to claim 1, wherein the respiratory diseases are pulmonary diseases accompanied by symptoms of cough, sputum, dyspnea, airway hypersensitivity, airway obstruction, mucus hypersecretion, decreased expiratory flow rate and/or gas exchange disorder.

3. The food composition according to claim 1, wherein the respiratory diseases are asthma, chronic obstructive pulmonary disease (COPD), diffuse interstitial pulmonary disease, acute respiratory distress syndrome (ARDS), or acute lung injury.

4. The food composition according to claim 3, wherein the respiratory diseases are the asthma or the COPD.

5. A health functional food comprising the food composition according to claim 1.

6. A pharmaceutical composition for preventing or treating respiratory diseases, comprising:

Lactobacillus plantarum KF511 strain (*L. plantarum* KF511);
a culture solution comprising *L. plantarum* KF511;
a concentrate comprising *L. plantarum* KF511; or
a dried product comprising *L. plantarum* KF511;
wherein the pharmaceutical composition comprises $10^7$ to $10^{12}$ CFU of the *L. plantarum* KF511, the *L. plantarum* KF511 is an active ingredient in the pharmaceutical composition and is assigned an accession number KCCM 12573P.

7. The pharmaceutical composition according to claim 6, wherein the respiratory diseases are asthma, chronic obstructive pulmonary disease (COPD), diffuse interstitial pulmonary disease, acute respiratory distress syndrome (ARDS), or acute lung injury.

8. The pharmaceutical composition according to claim 7, wherein the respiratory diseases are the asthma or the COPD.

* * * * *

SEQUENCE LISTING

```
<160> NUMBER OF SEQ ID NOS: 1

<210> SEQ ID NO 1
<211> LENGTH: 1499
<212> TYPE: DNA
<213> ORGANISM: Lactobacillus plantarum

<400> SEQUENCE: 1
ggctcaggac gaacgctggc ggcgtgccta atacatgcaa gtcgaacgaa ctctggtatt        60
gattggtgct tgcatcatga tttacatttg agtgagtggc gaactggtga gtaacacgtg       120
ggaaacctgc ccagaagcgg gggataacac ctggaaacag atgctaatac cgcataacaa       180
cttggaccgc atggtccgag tttgaaagat ggcttcggct atcacttttg gatggtcccg       240
cggcgtatta gctagatggt ggggtaacgg ctcaccatgg caatgatacg tagccgacct       300
gagagggtaa tcggccacat tgggactgag acacggccca aactcctacg ggaggcagca       360
gtagggaatc ttccacaatg gacgaaagtc tgatggagca acgccgcgtg agtgaagaag       420
ggtttcggct cgtaaaactc tgttgttaaa gaagaacata tctgagagta actgttcagg       480
tattgacggt atttaaccag aaagccacgg ctaactacgt gccagcagcc gcggtaatac       540
gtaggtggca agcgttgtcc ggatttattg ggcgtaaagc gagcgcaggc ggttttttaa       600
gtctgatgtg aaagccttcg gctcaaccga agaagtgcat cggaaactgg gaaacttgag       660
tgcagaagag gacagtggaa ctccatgtgt agcggtgaaa tgcgtagata tatggaagaa       720
caccagtggc gaaggcggct gtctggtctg taacctgacg ctgaggctcg aaagtatggg       780
tagcaaacag gattagatac cctggtagtc cataccgtaa acgatgaatg ctaagtgttg       840
gagggtttcc gcccttcagt gctgcagcta acgcattaag cattccgcct ggggagtacg       900
gccgcaaggc tgaaactcaa aggaattgac ggggcccgc acaagcggtg gagcatgtgg       960
tttaattcga agctacgcga agaaccttac caggtcttga catactatgc aaatctaaga      1020
gattagacgt tcccttcggg gacatggata caggtggtgc atggttgtcg tcagctcgtg      1080
tcgtgagatg ttgggttaag tcccgcaacg agcgcaaccc ttattatcag ttgccagcat      1140
taagttgggc actctggtga gactgccggt gacaaaccgg aggaaggtgg ggatgacgtc      1200
aaatcatcat gccccttatg acctgggcta cacacgtgct acaatggatg gtacaacgag      1260
ttgcgaactc gcgagagtaa gctaatctct taaagccatt ctcagttcgg attgtaggct      1320
gcaactcgcc tacatgaagt cggaatcgct agtaatcgcg gatcagcatg ccgcggtgaa      1380
tacgttcccg ggccttgtac acaccgcccg tcacaccatg agagtttgta acacccaaag      1440
tcggtggggt aaccttttag gaaccagccg cctaaggtgg gacagatgat tagggtgaa       1499
```